(12) United States Patent
Dal Farra et al.

(10) Patent No.: US 7,737,119 B2
(45) Date of Patent: *Jun. 15, 2010

(54) COSMETIC OR PHARMACEUTICAL COMPOSITION COMPRISING PEPTIDES, USES AND TREATMENT PROCESSES

(75) Inventors: Claude Dal Farra, Opio (FR); Nouha Domloge, Valbonne (FR); Jean-Marie Botto, Valbonne (FR)

(73) Assignee: Societe d'Extraction des Principes Actifs S.A., Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/134,795

(22) Filed: Jun. 6, 2008

(65) Prior Publication Data

US 2009/0012002 A1   Jan. 8, 2009

Related U.S. Application Data

(63) Continuation-in-part of application No. 10/508,245, filed as application No. PCT/FR03/00817 on Mar. 14, 2003, now Pat. No. 7,396,815.

(30) Foreign Application Priority Data

Mar. 18, 2002 (FR) .................................. 02 03306
Feb. 6, 2008 (FR) .................................. 08 00611

(51) Int. Cl.
*A61K 38/10* (2006.01)
*A61K 38/08* (2006.01)
*A61K 8/02* (2006.01)

(52) U.S. Cl. ..................... 514/14; 514/16; 530/329; 530/326; 424/401

(58) Field of Classification Search ........................ None
See application file for complete search history.

(56) References Cited

U.S. PATENT DOCUMENTS 5,696,229 A   12/1997   Matter et al.
6,245,342 B1   6/2001   Golz-Berner et al.

FOREIGN PATENT DOCUMENTS

WO   WO 99/42126   8/1999
WO   WO 01/83516 A1   11/2001

OTHER PUBLICATIONS

Patent Abstracts of Japan, vol. 011, No. 085 (C-410), Mar. 14, 1987 & JP 61 2387 12 A (Shiseido Co Ltd), Oct. 24, 1986 abstract.
C. Dal Farra et al.: "Development of a new fibronectin peptide, and its effect on epidermal cell adhesion", Molecular Biology of the Cell, Nov. 2001, p. 190a XP008012370, abrege n 1033O.
C. Dal Farra et al.: "New laminin-peptide promotes extracellular matrix production and modulates cell adhesion", Journal of Investigative Dermatology, vol. 119, No. 1 Jul. 2002, p. 231 XP008012371, Malden, MA US ABREGE N 140.

*Primary Examiner*—Andrew D Kosar
*Assistant Examiner*—Satyanarayana R Gudibande
(74) *Attorney, Agent, or Firm*—Young & Thompson

(57) ABSTRACT

The present invention has as an aim a cosmetic and/or dermatological and/or pharmaceutical composition comprising, as an active ingredient, at least a peptide of sequence $X_1$-Y-Phe-Thr-$X_2$-Ala-Thr-Z-Ile-$X_3$-Leu-$X_4$-Phe-Leu-$X_5$ (SEQ ID NO: 1); wherein: $X_1$, $X_2$, $X_3$, $X_4$, $X_5$=Arg, Lys, His; Y=Asp, Glu; Z=Asn, Gln, or one of its fragment containing from 4 to 7 amino acids, and the motif Phe-Leu.

The invention also relates to a method for preventing or treating skin against the manifestations of cutaneous aging.

19 Claims, No Drawings

SEQUENCE LISTING

```
<160> NUMBER OF SEQ ID NOS: 11

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Arg, Lys or His
<220> FEATURE:
<221> NAME/KEY: MOD_RES
<222> LOCATION: (2)
<223> OTHER INFORMATION: Asp or Glu
<220> FEATURE:
<221> NAME/KEY: MOD_RES
<222> LOCATION: (5)
<223> OTHER INFORMATION: Arg, Lys or His
<220> FEATURE:
<221> NAME/KEY: MOD_RES
<222> LOCATION: (8)
<223> OTHER INFORMATION: Asn or Gln
<220> FEATURE:
<221> NAME/KEY: MOD_RES
<222> LOCATION: (10)
<223> OTHER INFORMATION: Arg, Lys or His
<220> FEATURE:
<221> NAME/KEY: MOD_RES
<222> LOCATION: (12)
<223> OTHER INFORMATION: Arg, Lys or His
<220> FEATURE:
<221> NAME/KEY: MOD_RES
<222> LOCATION: (15)
<223> OTHER INFORMATION: Arg, Lys or His

<400> SEQUENCE: 1

Xaa Xaa Phe Thr Xaa Ala Thr Xaa Ile Xaa Leu Xaa Phe Leu Xaa
 1               5                  10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Arg, Lys or His
<220> FEATURE:
<221> NAME/KEY: MOD_RES
<222> LOCATION: (4)
<223> OTHER INFORMATION: Arg, Lys or His
<220> FEATURE:
<221> NAME/KEY: MOD_RES
<222> LOCATION: (7)
<223> OTHER INFORMATION: Arg, Lys or His

<400> SEQUENCE: 2

Ile Xaa Leu Xaa Phe Leu Xaa
 1               5
```

```
<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Asp Phe Thr Lys Ala Thr Asn Ile Arg Leu Arg Phe Leu Arg
 1               5                  10                  15

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Arg Leu Arg Phe Leu Arg
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 5

Ile Arg Leu Arg Phe Leu Arg
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Lys Leu Arg Phe Leu His
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 7

Ile Lys Leu Arg Phe Leu His
 1               5

<210> SEQ ID NO 8
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 8

Ile His Leu Lys Phe Leu Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 9

Ile His Leu Lys Phe Leu Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Lys Leu His Phe Leu Lys
1               5

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Phe Thr Lys Ala Thr Asn Ile Arg Leu Arg Phe Leu Arg
1               5                   10
```

COSMETIC OR PHARMACEUTICAL COMPOSITION COMPRISING PEPTIDES, USES AND TREATMENT PROCESSES

The present application claims the 35 U.S.C. §120 benefit of prior copending U.S. patent application Ser. No. 10/508,245 filed Sep. 20, 2004, which is incorporated herein by reference, and to which the present application is a continuation-in-part US national non-provisional utility patent application.

The present invention refers to the pharmaceutical field, and more particularly the field of the dermatology like that of the cosmetics. The present invention has as an aim a cosmetic and/or dermatological and/or pharmaceutical composition comprising, as an active ingredient, at least a peptide of formula (I) $X_1$-Y-Phe-Thr-$X_2$-Ala-Thr-Z-Ile-$X_3$-Leu-$X_4$-Phe-Leu-$X_5$ (SEQ ID NO:1); wherein: $X_1$, $X_2$, $X_3$, $X_4$, $X_5$=Arg, Lys or His; Y=Asp or Glu; Z=Asn or Gln, or one of its C terminal fragments, consisting in a peptide of 7 amino acid residues bearing the Phe-Leu motif, of formula (II) Ile-$X_3$-Leu-$X_4$-Phe-Leu-$X_5$ (SEQ ID NO: 2), wherein: $X_3$, $X_4$, $X_5$=Arg, Lys or His.

The invention also relates to a method for preventing or treating skin against the manifestations of cutaneous aging.

The skin is a coating organ covering the totality of the body's surface. It is a vital organ ensuring multiple functions such as sensitive, protective functions from external aggressions, immunological, metabolic or thermoregulatory functions. These roles are made possible due to a complex structure which associates varied tissue structures.

Skin, like all the other organs, is subjected to aging. The first general manifestation of cutaneous aging is the appearance of fine lines. The skin becomes less flexible, finer, often dry and it loses its elasticity. The loss of flexibility, firmness and hydration of the skin, as well as the appearance of wrinkles and fine lines are due, probably, to the unequal loss of the various types of macromolecules of the cutaneous matrix.

The dermo-epidermal junction is a complex structure which represents an interface zone between the dermis and the skin. It is composed of the basal pole of the keratinocytes as well as the basal layer, a specialized structure of the extracellular matrix.

The synthesis of the basal layer is early altered during aging, and thus a decrease in the synthesis of the molecules which compose it, is observed, as well as an increase of the enzyme activities which degrade it. Cell adhesion and cell communication between the dermis and the skin thus decrease in the same manner. (*Gilchrest B A. Skin aging and photoaging: an overview. J Am Acad Dermatol.* 21: 610-3, 1989.).

The basal layer consists of macromolecules which play a primordial role, in particular in the anchoring phenomena and cellular differentiation; among the proteins which compose it, we can quote laminine, collagen, fibronectin or elastin.

As a key element of the extracellular matrix, laminine takes part in the cell adhesion and intercellular cement. To provide these adhesion functions, laminins bind to transmembrane receptors such as integrins. This interaction initiates, in the same way, cellular communication, cellular differentiation, migration or cellular proliferation.

The specialists of health and cosmetics have been seeking for many years means to fight or, at least, to reduce cutaneous aging, as well as means to increase the resistance of the skin to the external aggressions and stress to which it is daily exposed. A certain number of substances are used in cosmetics or pharmaceutical products were born, but there still remains progress to make in order to be able to have cosmetic or pharmaceutical products able to regulate these problems satisfactorily.

The technical problem to solve was, for the inventors, to find a cosmetically or pharmaceutically acceptable new substance, which is able to fight the cutaneous aging phenomenon and, in particular, to act on the cell adhesion phenomenon.

However, the inventors succeeded in selecting particular substances presenting remarkable properties when applied to the skin, such as properties at the level of the extracellular matrix, and more particularly at the level of the basal layer.

The inventors unexpectedly discovered that the peptides corresponding to the general formula I, (SEQ ID NO: 1): $X_1$-Y-Phe-Thr-$X_2$-Ala-Thr-Z-Ile-$X_3$-Leu-$X_4$-Phe-Leu-$X_5$, wherein: $X_1$, $X_2$, $X_3$, $X_4$, $X_5$=Arg, Lys or His; Y=Asp or Glu; Z=Asn or Gln, or one of its C terminal fragments, consisting in a peptide of 7 amino acid residues bearing the Phe-Leu motif, of formula (II) (SEQ ID NO: 2): Ile-$X_3$-Leu-$X_4$-Phe-Leu-$X_5$, wherein: $X_3$, $X_4$, $X_5$=Arg, Lys or His, have remarkable properties and that they help prevent cutaneous aging phenomena. The applicant thus discovered a product which has an effect on the production of proteins essential to the skin, such as extracellular matrix proteins.

To the knowledge of the applicant, it was never described in former art the use of a peptide of sequences SEQ ID NO: 1 or SEQ ID NO: 2 in the cosmetic and/or dermatology and/or pharmaceutical field.

Thus, according to a first aspect, the object of the present invention is a cosmetic and/or dermatological and/or pharmaceutical composition characterized by the fact that it contains, as an active ingredient, an effective quantity of at least a peptide of formula (I):

(SEQ ID NO: 1)
$X_1$-Y-Phe-Thr-$X_2$-Ala-Thr-Z-Ile-$X_3$-Leu-$X_4$-Phe-Leu-$X_5$, wherein:
$X_1$, $X_2$, $X_3$, $X_4$, $X_5$=Arg, Lys or His;
Y=Asp or Glu;
Z=Asn or Gln.
or one of its C terminal fragments, consisting in a peptide of 7 amino acid residues bearing the Phe-Leu motif, of formula (II)

(SEQ ID NO: 2)    Ile-$X_3$-Leu-$X_4$-Phe-Leu-$X_5$ wherein:
$X_3$, $X_4$, $X_5$=Arg, Lys or His.

According to another mode of realization, the above mentioned peptide is preferentially the peptide of sequence SEQ ID NO: 3:
Arg-Asp-Phe-Thr-Lys-Ala-Thr-Asn-Ile-Arg-Leu-Arg-Phe-Leu-Arg.

In another advantageous embodiment, the above mentioned fragments of formula (II) comprises or consists of the following sequences:

(SEQ ID NO: 4)    Ile-Arg-Leu-Arg-Phe-Leu-Arg (SEQ ID NO: 5)    Ile-Arg-Leu-Arg-Phe-Leu-Arg-$NH_2$ (SEQ ID NO: 6)    Ile-Lys-Leu-Arg-Phe-Leu-His

-continued (SEQ ID NO: 7)  Ile-Lys-Leu-Arg-Phe-Leu-His-NH$_2$ (SEQ ID NO: 8)  Ile-His-Leu-Lys-Phe-Leu-Arg (SEQ ID NO: 9)  Ile-His-Leu-Lys-Phe-Leu-Arg-NH$_2$ (SEQ ID NO: 10) Ile-Lys-Leu-His-Phe-Leu-Lys In another advantageous embodiment, the peptide has the sequence SEQ ID NO: 4.

In another advantageous embodiment, the peptide has the sequence SEQ ID NO: 5.

It may be that for questions of resistance to degradation, it is necessary to use a protected form of the peptide. The form of protection must obviously be a biologically compatible form and must be compatible with a use in the cosmetics or pharmacy field.

Thus, the invention refers to a use of peptide, such as previously defined, characterized by the fact that the peptide is in a protected form or not. Many biologically compatible forms of protection can be used, for example, the acylation or the acetylation of the amino-final end, or the amidation or the esterification of the carboxy-terminal end, or either both.

Preferably, we use a protection of the peptide based on the amidation of the carboxy-terminal end.

In the field of amino acids, the geometry of the molecules is such that they can theoretically appear as different optical isomers. There is indeed a molecular conformation of the amino acid (aa) such as it deviates on the right the plan of light polarization (dextrogyre conformation or D-aa), and a molecular conformation of the amino acid such as it deviates on the left the plan of light polarization (levogyre conformation or L-aa). Nature retained for the natural amino acids only levogyre conformation. Consequently, a peptide of natural origin will be made only with amino acids of L-aa type.

However, the chemical synthesis in laboratory makes it possible to prepare amino acids having two possible conformations. From this basic material, it is thus possible during the peptide synthesis to incorporate amino acids in the form of dextrogyre or levogyre optical isomers.

Thus, the amino acids constituting the peptide relating to the invention, can be in L- and D-configuration; in a preferential way, the amino acids are in L-form. The peptide relating to the invention can thus be in L-, D- or DL-form.

Peptides, object of this patent, can be obtained either by traditional chemical synthesis (in solid phase or in homogeneous liquid phase), or by enzymatic synthesis (Kullman et al., *J. Biol. Chem.* 1980, 225, 8234) from constitutive amino acids or of their derivatives.

Peptides relating to the invention can also be obtained by fermentation of a stock of bacteria modified or not by genetic engineering to produce peptides of sequence, as previously indicated, and their fragments, or by protein extraction of animal or vegetable origin, followed by controlled hydrolysis which releases the peptide fragments in question of average size and of small size.

It is possible, but not necessary to carry out the invention, to extract either proteins concerned initially and to hydrolyze them, or to initially carry out the hydrolysis on rough extract and then to purify the peptide fragments.

Other simpler or more complex processes can be considered by the specialists in their field, knowing the work of synthesis, extraction and purification of proteins and peptides.

Thus the peptide relating to the invention can be a peptide of a natural or synthetic origin. Preferentially relating to the invention, the peptide is obtained by chemical synthesis.

In addition, it is clearly established that the invention also relates to all proteins or proteins fragments containing the peptide of sequence SEQ ID NO: 1 or SEQ ID NO: 2.

When we use a polypeptide containing the aforementioned peptide, it is clearly established that this one is selected so that the amino acids surrounding it, both by their nature and the secondary structure of the peptide they will induce, do not prevent it from carrying on the activity for which it is used in the present invention.

According to the present invention, the composition can be a cosmetic or dermatological or pharmaceutical composition. Preferentially relating to the invention, the composition is a cosmetic composition, since it is aimed at improving the cutaneous appearance and general cutaneous performance of the individual who uses it.

According to the present invention, the composition is preferably a cosmetic and/or dermatological composition adapted for topical cutaneous application through an acceptable cosmetic or dermatological medium.

The term "topical cutaneous application" relates to an application by direct spreading of the composition disclosed in the invention, at the surface of the skin, mucous membranes, hair scalp or nails.

The term "acceptable cosmetic or dermatological medium" relates to a medium that is compatible with skin, mucous membranes, hair, and nails.

It is evident that the invention relates to mammals in general, and more specifically, to humans.

The effective quantity of above mentioned peptide, as active ingredient, corresponds to the quantity necessary to obtain the desired result.

Relating to an advantageous mode of realization of the invention, the above mentioned peptide is present in the compositions of the invention at a concentration from 0.005 to 500 ppm (p/p) approximately and preferentially at a concentration from 0.1 to 50 ppm (p/p) approximately.

Relating to an advantageous mode of realization of the invention, the above mentioned peptide is solubilized beforehand in one or several solvents cosmetically or pharmaceutically acceptable such as water, glycerol, ethanol, propanol or isopropanol, propylene glycol, butylene glycol, dipropylene glycol, ethoxylated or propoxylated diglycols, cyclic polyols, vaseline, vegetal oil or any combinations of these solvents.

Relating to another advantageous mode of realization of the invention, the above mentioned peptides are beforehand solubilized in a cosmetic or pharmaceutical vector such as liposomes or are adsorbed on powdered organic polymers, mineral supports such as talc and bentonites, and more generally solubilized in, or fixed on, any cosmetically or pharmaceutically acceptable vectors.

Whatever form the invention takes, the composition, according to the invention can be ingested, injected, or, applied on skin (on all cutaneous zones of the body), hair, nails or mucous membranes. According to the mode of administration, the composition related to the invention can be presented under all galenic forms normally used.

The compositions related to the invention are preferably presented under a galenic form adapted for cutaneous topical administration. They cover all the cosmetic and dermatological forms. These compositions must contain an acceptable cosmetic or dermatological medium. That is to say, a medium that is compatible with skin and hair.

These compositions can take the form of an aqueous, hydra-alcoholic, or oil solution in oil-water emulsions, wateroil emulsions or in multiple emulsions. They can also be used as creams, in suspension, or as a powder, as long as it is adapted for application on skin, mucous membranes, lips and/or hair.

These compositions can also be more or less fluid and take the form of creams, lotions, milks, serums, ointments, shampoo, gel, paste and mousse. It can also take a solid form like a stick, or it can be used in aerosols. It can also be used as a skin care product and/or as make-up for skin.

Concerning injection, the composition related to the invention can be an aqueous or oil based lotions or a serum. For application on the eyes, the composition can be used as drops whereas for ingestion it can be used as capsules, granules, syrup or pills.

Moreover, these compositions represent all of the additives that are usually considered for use in this application. These compositions also represent all the possible additives necessary for their formulation such as solvents, thickeners, diluents, anti-oxidants, colorants, solar filters, auto-tanning products, pigments, fillers, preservatives, perfumes, odor absorbers, pharmaceutical and cosmetic active ingredients, essential oils, vitamins, essential fatty acids, tensioactivators, filmogen polymers etc. . . .

In all of these cases, specialists in their field will want to carefully consider the selection of adjuvants, as well as their proportions, so as not to compromise the advantageous properties of the composition relating to the invention. These adjuvants can, for example, correspond to 0.01% to 20% of the total weight of the composition.

When the composition related to the invention is in an emulsion, the fatty phase can represent 5% to 80% by weight, but preferably it would represent 5% to 50% of the weight with respect to the total weight of the composition. Emulsifiers or co-emulsifiers used in the composition are selected among those that are classically used in the domain under consideration. For example, they can be used in a proportion of 0.3% to 30% by weight relative to the total weight of the composition.

Of course, the specialists in their field should select the complementary compounds for the composition, active or non-active, as well as the amounts of the complementary compounds in such a way that the advantageous properties of the composition will not be perceptibly altered by the envisaged addition.

The compositions related to the present invention can be applied most notably as a cosmetic or pharmaceutical composition for use on skin, mucous membranes and/or semi-mucous membranes.

The compositions can be applied particularly in so far as skin protection and skin care products are concerned, or as an anti-wrinkle and/or an anti-aging composition.

We can also consider an application in the field of facial and body make-up compositions, such as lipsticks, foundation, tinted creams, dark circle sticks, or sunscreen and artificial tanning compositions.

The compositions of the invention can be used in a great number of treatments, notably cosmetic and dermatological. They can take the form of cosmetic compositions used for skin, lips and/or hair treatment, protection, care and make-up removal and/or cleaning, as well as for make-up applications on skin, lips, eye lashes and/or the body.

The composition relating to the invention can also consist of solid preparations such as soap and other cleaning bar soaps.

The composition can also be made in aerosol form in which it can be mixed with pressurized propulsion agents.

The composition can also be formulated in an appropriate form to be administered orally intended for a pharmaceutical or a cosmetic use. These compositions can take the form of drinkable solution, syrups, tablets, chewable gums, sugar coated pills, capsules, toothpastes, or even as food and nutritional supplements.

In another embodiment of the invention, likewise we can add to the composition of the invention, other active agents intended to promote the action of the above mentioned peptide for the prevention and/or treatment of the manifestations of cutaneous aging. Among these other active ingredients we can cite moisturizing agents, lightening agents, smoothing agents and anti-wrinkle agents.

Another object of the invention is the use, as an active ingredient, of at least a peptide of sequence SEQ ID NO: 1, $X_1$-Y-Phe-Thr-$X_2$-Ala-Thr-Z-Ile-$X_3$-Leu-$X_4$-Phe-Leu-$X_5$, wherein: $X_1$, $X_2$, $X_3$, $X_4$, $X_5$=Arg, Lys or His; Y=Asp or Glu and Z=Asn or Gln; in prone of its C terminal fragments, consisting in a peptide of 7 amino acid residues, of SEQ ID NO: 2, Ile-$X_3$-Leu-$X_4$-Phe-Leu-$X_5$, wherein $X_3$, $X_4$, $X_5$=Arg, Lys or His, for the preparation of a cosmetic and/or dermatological and/or pharmaceutical composition.

It was observed that the peptide relating to the invention has many actions in the skin, in particular it makes it possible to fight against the cutaneous aging phenomena and enables the skin to be protected against all types of external aggressions.

In addition, the aforementioned active agent increases the expression of skin proteins and/or improves their stability. Peptides relating to the invention thus promote tissue regeneration, by increasing the cell differentiation phenomenon, and it thus reinforces the function barrier of the skin.

Another object of the invention is the use of at least one peptide of formula (I), SEQ ID NO: 1, or formula (II), SEQ ID NO: 2, such as previously defined, or of a cosmetic composition comprising it, in order to fight in a curative and/or preventive way, against the signs of cutaneous aging, but also in order to improve the skin's aspect.

The phrase "to improve the appearance of the skin" refers to all the phenomena which are likely to have for consequences a visual improvement of the state of the skin. The skin will have a better appearance; it will be, for example, much more beautiful, firm and/or smooth. All the small imperfections will be decreased or removed. The papyraceous aspect of the skin, for example, will be attenuated.

Manifestations of cutaneous aging include all of the modifications regarding external appearance of skin due to aging. Examples of these modifications include wrinkles and fine lines, limp skin, slackened skin, slimmer looking skin, loss of elasticity and/or skin tone, dull skin, and skin which lacks radiance. It also includes internal skin modifications that do not translate directly as changes in external skin appearance. An example of these internal modifications is the degradation that occurs internally in skin resulting from consecutive exposure to UV radiation.

It was highlighted many properties of the composition according to the invention. Indeed, such as the experiments show it in the examples, peptides of formula (I), SEQ ID NO: 1, or formula (II), SEQ ID NO: 2, have beneficial effects on the protein synthesis of the extracellular matrix.

Another objective of the invention is the use of at least a peptide such as defined previously, or of a cosmetic composition including it, in order to increase the protein expression of the extracellular matrix.

There may be mentioned, by way of example of proteins of the extracellular matrix, proteins such as collagen, fibronectin, laminin. All these proteins are constitutive of the matrix and play a fundamental role, and particularly play an important part in cell adhesion.

More specifically, the peptide or the composition according to the invention allows for the increase in the expression of laminin; in particular, they make it possible to increase laminin-5 synthesis. This protein, for example, interacts with the integrins of basal keratinocytes, which permit thus to anchor the cells on the two-dimensional network of the dermo-epidermal junction.

According to another aspect, the peptide or the composition relating to the invention allows the integrin synthesis to increase, in particular the expression of the subunits α6 et β1.

Cell adhesion is carried out, in particular, by integrins. These proteins interact with various molecules of the extracellular matrix, like fibronectin or laminin. They are involved in the keratinocyte adhesion to the extracellular matrix, in the connections between cells and in the basement membrane cohesion of the skin. Thus, an increase in the adherent capacity of the cutaneous cells can indicate an increase of the integrin expression.

The peptide according to the invention, while inducing an increase in the integrin expression, will thus induce an increase in the capacity of adherence of the cutaneous cells.

Thus, the invention has for another object the use in or for the preparation of a cosmetic or dermatological composition, of an effective quantity of peptides of formula (I), SEQ ID NO: 1, or formula (II), SEQ ID NO: 2; the peptides or the composition are likely to increase cell adhesion. More particularly, peptides or the composition are intended to increase the adhesion of the cutaneous cells.

The phrase "cell adhesion" on the one hand refers to cell-extracellular matrix adhesion and, on the other hand, cell-cell adhesion. The phrase "adhesion of cutaneous cells" on the one hand refers to cutaneous cell-extracellular matrix adhesion, on the other hand, cell-cell adhesion.

In addition, the dynamic of cell adhesion is related to the mechanical properties of the extracellular matrix. The creation of an extracellular matrix very rich in proteins which compose it, in particular rich in fibronectin, facilitates the phenomenon of re-epithelization. Re-epithelization is the term used to describe the renewal of the skin by a new epithelium of keratinocytes. This process utilizes complex biological mechanisms and requires the presence of molecules of adhesions as well as the presence of an extracellular matrix. The peptide relating to the invention thus facilitates the re-epithelization process and wound healing of the skin.

Another aspect of the invention is thus the use in or for the preparation of a composition, of an effective quantity of peptides such as previously defined; the peptides or the composition are likely to accelerate wound healing and tissue regeneration. The composition according to the invention is thus used for the tissue regeneration of the skin and/or nails in general.

The peptide and the composition, relating to the invention, thus present interesting properties with respect to the skin and/or nails, in particular of the properties of tissue regeneration which allow, for example, a wound improved healing as well as anti-aging properties making it possible to prevent and/or reduce the effects related to skin aging.

The composition permits the organization of the skin, and contributes to a protection of the deepest layers. The skin becomes thicker, deeper and is in continual interaction with the dermis.

Thus, the peptide according to the invention reinforces the function barrier of the skin and, it makes it possible, in particular, to protect the skin and/or the hair in an effective way against all types of external aggressions.

The phrase "external aggressions" refers to the aggressions which the environment can produce. These aggressions can be of chemical, physical, biological or thermal origin. As an example, we can quote aggressions such as pollution, UV, frictions, water with strong limestone concentration, variations in temperature or potentially irritating products such as tensioactives, preservatives or fragrances.

According to another aspect, the present invention relates to a cosmetic process of treatment to treat old skins and/or to fight aging phenomena and/or to improve the skin's appearance consisting in applying, to the surface of the skin or the hair, an effective quantity of at least a peptide corresponding to the formula (I), SEQ ID NO: 1, or formula (II), SEQ ID NO: 2, in order to obtain the desired action.

In the same way, the present invention relates to a cosmetic process of treatment in order to reinforce the function barrier of the skin and/or to protect the skin and the hair against all types of external aggression.

The present invention also relates to a cosmetic process of treatment in order to increase cell adhesion, consisting in applying to the skin the composition such as previously defined.

According to another aspect of the invention, the present invention relates to a cosmetic process of treatment in order to promote tissue regeneration and/or in order to accelerate skin wound healing.

The invention also relates to a cosmetic process in order to increase the molecule expression of the extracellular matrix and/or the integrin expression, consisting in applying to the skin the composition such as previously defined.

Particular modes of realization of this process of cosmetic treatment also result from the preceding description.

The process of cosmetic treatment related to the invention can be implemented in particular by applying the cosmetic compositions here above according to methods habitually used for compositions such as the application of creams, gels, serums, lotions, milks, shampoo, and sun creams, on skin, hair and as a toothpaste applied to the gums.

Other advantages and characteristics of the invention will become apparent by reading the following examples, by way of an illustrative and unrestrictive demonstration of data.

EXAMPLE 1

Study of the stability of peptide SEQ ID NO: 3, Arg-Asp-Phe-Thr-Lys-Ala-Thr-Asn-Ile-Arg-Leu-Arg-Phe-Leu-Arg.

Peptide SEQ ID NO: 3 Arg-Asp-Phe-Thr-Lys-Ala-Thr-Asn-Ile-Arg-Leu-Arg-Phe-Leu-Arg was analyzed with a concentration of $10^{-4}$ M by HPLC on a C18 type column, and with a linear gradient water/TFA 0.1%-acetonitrile/TFA 0.1%. After 24 hours at various temperatures (25° C., 37° C. and 60° C.), no degradation of the peptide was observed. Moreover, after 8 days at 25° C., the peptide still does not present degradation.

Human fibroblasts and keratinocytes were cultured during 24 hours at 37° C. and to 5% of $CO_2$. For this period, the cells will release numerous enzymes of degradation in the culture medium. Thereafter, the culture medium is withdrawn to be put in the presence of peptide. The results of the performed analyses show that after 24 hours the peptide presents almost no degradation.

A test is performed by applying the peptide to fibroblasts as well as to human keratinocytes in culture. A HPLC analysis of the culture medium reveals that the peptide concentration decreases quickly, that is to say in a few hours.

These results, taken as a whole, suggest a very good stability of the peptide SEQ ID NO: 3 in the course of time as well as the possibility of a penetration of the peptide in the cell. This assumption is then consolidated by the efficacy tests exposed in the following examples.

EXAMPLE 2

Description of the effect of the peptide SEQ ID NO: 3 on adhesion between cutaneous cells.

The study is performed in 96 well micro-plates on keratinocytes cultured in an incubator at 37° C. and 5% of $CO_2$.

The wells are pre-treated during 12 hours in a different way; four conditions are thus performed:
 Condition A: negative control, containing no peptide;
 Condition B: incubated with various peptides, made of 3 to 25 amino acids (from the extracellular matrix), with a concentration from 5 to 50 ppm;
 Condition C: incubated with the peptide of sequence Arg-Asp-Phe-Thr-Lys-Ala-Thr-Asn-Ile-Arg-Leu-Arg-Phe-Leu-Arg (SEQ ID NO: 3) to a concentration of 5 ppm.

After 3 hours of contact with the keratinocytes, the wells are completely filled with culture medium, hermetically closed, turned over and agitated on a three-dimensional agitator during 20 minutes. Then the plates are emptied and the medium remaining is aspired. 100 µl of MTT with 1 mg/ml per well is added and is left during 3 hours at 37° C. and 5% of $CO_2$. The solution is finally withdrawn and 100 µl of DMSO is added. A reading of C is made at 560 nm against 630 nm.

The results present the various Optical Density (O.D.) obtained according to the various conditions. The O.D. is proportional to the quantity of viable cells, that is to say those which adhered to the micro-plates.

|      | Conditions |      |      |
| ---- | ---------- | ---- | ---- |
|      | A          | B    | C    |
| O.D. | 0.36       | 0.36 | 0.43 |

These results show that after only 3 hours of contact with the keratinocytes, the peptide of sequence Asp-Phe-Thr-Lys-Ala-Thr-Asn-Ile-Arg-Leu-Arg-Phe-Leu-Arg (SEQ ID NO: 11) promotes a very good cell adhesion, quite higher than that of other peptides tested.

EXAMPLE 3

Immunofluorescence study of the effect of the peptide SEQ ID NO: 5 on fibronectin and type I and III collagen expression.

The purpose of the study is to determine the influence of the peptide SEQ ID NO: 5 on the fibronectin synthesis and on the type I and III collagen synthesis by immunofluorescence staining.

The immunofluorescence is a semi-quantitative technique which makes it possible to appreciate the rate of each protein present in the cellular cytoplasm.

Human fibroblasts are plated in Labteks then cultured for one night. After rinsing with HBS buffer, a composition containing 1% of a solution at 100 ppm of the peptide SEQ ID NO: 5, or a control composition containing no peptide, is added. The cells are then incubated for 48 hours. After performing the elimination of the supernatants and rinsing the cultures, the cells are fixed with paraformaldehyde for 30 minutes at 4° C. then rinsed with PBS buffer.

200 µL of anti-fibronectin antibody or anti-collagen I, or anti-collagen III polyclonal antibody obtained in the rabbit (TEBU) are then added. Incubation lasts 30 minutes at room temperature. The supernatants are eliminated and the cells are rinsed with PBS. 200 µL of secondary antibody, coupled to a fluorescent marker (Alexa-fluor 488) are then added. After 30 minutes of incubation at room temperature, the supernatants are eliminated and the cells are rinsed with the PBS.

The slides are then assembled and examined under epi-fluorescence microscope (Nikon Eclipse E600). The quantities of fibronectine and/or collagen of the type I and III, synthesized by the cells, are proportional to fluorescence intensity.

When the fibroblasts are incubated in the presence of the composition containing the peptide SEQ ID NO: 5, we observe an increase of fluorescence intensity at the end of 48 hours in the three experiments.

The results obtained show that the peptide SEQ ID NO: 5 increases the fibronectin synthesis and the type I and III collagen synthesis by the cells. This stimulation was observed in a significant way.

EXAMPLE 4

Immunofluorescence study of the effect of the peptide SEQ ID NO: 5 on the laminin-5 expression and β1 integrin expression.

The purpose of the study is to determine the influence of the peptide SEQ ID NO: 5 on the laminin-5 synthesis and β1 subunits synthesis of the integrins, by the keratinocytes and immunofluorescence technique.

A study by immunofluorescence technique, identical to that of example 3, was performed on HaCat human keratinocytes, with anti-laminin-5 antibodies and/or β1 anti-integrin antibodies.

When the keratinocytes are incubated in the presence of the peptide SEQ ID NO: 5, we observe an increase in fluorescence intensity at the end of 48 hours.

The results obtained show that the peptide SEQ ID NO: 5, added to increase laminin-5 synthesis and/or β1 integrin synthesis by the cells. This stimulation was observed in a significant way.

EXAMPLE 5

Immunofluorescence study of the effect of the peptide SEQ ID NO: 4 on the keratins expression.

The purpose of the study is to determine the influence of the peptide SEQ ID NO: 4 on the keratin synthesis in human ex vivo skin samples and immunofluorescence technique.

A study by immunofluorescence technique, identical to that of Example 3, was performed on ex vivo human skin samples, with anti-keratin monoclonal antibody (Novocastra).

When the ex vivo skin samples are incubated in the presence of the peptide SEQ ID NO: 4, we observe an increase in fluorescence intensity at the end of 48 hours.

The results obtained show that the peptide SEQ ID NO: 4, added to ex vivo skin samples increases keratin expression by the keratinocytes. This stimulation was observed in a significant way.

EXAMPLE 6

Preparation of Compositions

1—Day Cream

| Commercial Names | INCI Names | % by weight |
|---|---|---|
| PHASE A | | |
| MONTANOV 68 | Cetearyl Alcohol (and) Cetearyl Glucoside | 5.00 |
| JOJOBA OIL | Simmondsia Chinensis (Jojoba) Seed Oil | 3.00 |
| VASELINE OIL | Paraffinum Liquidum (Mineral Oil) | 2.00 |
| SQUALANE | Squalane | 3.00 |
| CERAPHYL 368 | Ethylhexyl palmitate | 4.00 |
| CERAPHYL 41 | C12-C15 Alkyl Lactate | 3.00 |
| RAPITHIX A-60 | Sodium polyacrylate (and) Hydrogenated Polydecene (and) Trideceth-6 | 0.30 |
| PHASE B | | |
| GLYCERIN | Glycerin | 5.00 |
| ALLANTOÏN | Allantoin | 0.10 |
| DEMINERALIZED WATER | Aqua (Water) | qs 100 |
| PHASE C | | |
| ROKONSAL MEP | Phenoxyethanol (and) Methylparaben (and) Ethylparaben (and) Propylparaben | 0.50 |
| PHASE D | | |
| PEPTIDE SEQ ID n° 5 | | 0.1 ppm |
| PHASE E | | |
| PARFUM | Parfum (Fragrance) | qsp |

The constituents of phase A and phase B are heated separately at 70° C. under stirring. Emulsify phase A into phase B. Add phase D when mix is cooled down to about 50° C. under stirring. Cooling is pursued down to 40° C., then add peptide (Phase D). Perfume then cool to room temperature.

2—Anti-Aging Cream:

| Commercial Names | INCI Names | % by weight |
|---|---|---|
| Phase A | | |
| Montanov 68 | Cetearyl Alcohol (and) Cetearyl Glucoside | 6.00 |
| Squalane | Squalane | 3.00 |
| Cetiol SB 45 | Butyrospermum Parkii (Shea Butter) | 2.00 |
| Waglinol 250 | Cetearyl Ethylhexanoate | 3.00 |
| Amerchol L-101 | Mineral Oil (and) Lanolin Alcohol | 2.00 |
| Abil 350 | Dimethicone | 1.50 |
| BHT | BHT | 0.01 |
| Coenzyme Q10 | Ubiquinone | 0.10 |
| Phase B | | |
| Avocado oil | Persea Gratissima (Avocado) Oil | 1.25 |
| Phenonip | Phenoxyethanol (and) Methylparaben (and) Ethylparaben (and) Butylparaben (and) Propylparaben (and) Isobutylparaben | 0.75 |
| Phase C | | |
| Deminéralized water | Aqua (Water) | qsp |
| Butylene Glycol | Butylene Glycol | 2.00 |
| Glucam E10 | Methyl Gluceth-10 | 1.00 |
| Allantoin | Allantoin | 0.15 |
| Carbopol Ultrez 10 | Carbomer | 0.20 |
| Phase D | | |
| TEA | Triethanolamine | 0.18 |
| Phase E | | |
| Peptide SEQ ID n° 5 | | 1 ppm |
| GP4G | Water (and) Artemia Extract | 1.50 |
| Collaxyl | Water (and) Butylene Glycol (and) Hexapeptide-9 | 3.00 |
| Phase F | | |
| Perfume | Parfum (Fragrance) | qs |
| dying | | qs |

Phase A is heated at 65-70° C. Heat phase C to 65-70° C. Phase B is added to phase A and emulsified at about 45° C. The carbomer is neutralized in adding phase D. Phase E is added under gentle stirring, and cooling is pursued down to 25° C. Phase F is added if needed.

3—Day Cream Protection:

| Commercial Names | INCI Names | % by weight |
|---|---|---|
| Phase A | | |
| Emulium Delta | Cetyl alcohol (and) Glyceryl Stearate (and) PEG-75 Stearate (and) Ceteth-20 (and) Steareth-20 | 4.00 |
| Lanette O | Cetearyl Alcohol | 1.50 |
| D C 200 Fluid/100cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| Cegesoft PS6 | Vegetable Oil | 1.00 |
| Vitamin E | Tocopherol | 0.30 |
| Phenonip | Phenoxyethanol (and) Methylparaben (and) Ethylparaben (and) Butylparaben (and) Propylparaben (and) Isobutylparaben | 0.70 |
| Phase B | | |
| Demineralized water | Aqua | qs 100 |
| Glycerin | Glycerin | 2.00 |
| Carbopol EDT 2020 | Acrylates/C10-30 Alkyl Acrylate Crosspolymer | 0.15 |
| Keltrol BT | Xanthan Gum | 0.30 |
| Phase C | | |
| Sodium Hydroxide (sol. à 10%) | Sodium Hydroxide | 0.30 |
| Phase D | | |
| Demineralized water | Aqua | 5.00 |
| Stay-C 50 | Sodium Ascorbyl Phosphate | 0.50 |
| Phase E | | |
| Butylene Glycol | Butylene Glycol | 2.00 |
| Dekaben CP | Chlorphenesin | 0.20 |
| Phase F | | |
| GP4G | Water (and) Artemia Extract | 1.00 |
| Peptide SEQ ID n° 5 | | 5 ppm |

Prepare phase A by heating at 75° C. under stirring. Prepare phase B by dispersing carbopol, the xanthane gum under stirring. Leave. Heat at 75° C. and emulsify A and B with rotor-stator. Neutralize by the addition of phase C under high speed stirring. After cooling down to 40° C., add phase D, then phase E. The cooling is pursued down under gentle stirring and then phase F is added, while stirring.

What is claimed:

1. A cosmetic, pharmaceutical, or dermatological composition comprising, as an active ingredient, an effective quantity of at least one peptide consisting of formula (I):

$$X_1\text{-}Y\text{-}Phe\text{-}Thr\text{-}X_2\text{-}Ala\text{-}Thr\text{-}Z\text{-}Ile\text{-}X_3\text{-}Leu\text{-}X_4\text{-}Phe\text{-}Leu\text{-}X_5, \quad (\text{SEQ ID NO: 1})$$

wherein $X_1, X_2, X_3, X_4, X_5$=Arg, Lys or His,

Y=Asp or Glu, and Z=Asn or Gln; or a C terminal fragment of the peptide, consisting of seven amino acid residues bearing a Phe-Leu motif of formula (II):

$$\text{Ile-}X_3\text{-}Leu\text{-}X_4\text{-}Phe\text{-}Leu\text{-}X_5, \quad (\text{SEQ ID NO: 2})$$

wherein $X_3, X_4, X_5$=Arg, Lys or His, and optionally amidated at the C-terminal.

2. The composition according to claim 1, wherein the peptide of formula (I) consists of the sequence Arg-Asp-Phe-Thr-Lys-Ala-Thr-Asn-Ile-Arg-Leu-Arg-Phe-Leu-Arg (SEQ ID NO: 3).

3. The composition according to claim 1, wherein the peptide of formula (I) or formula (II) comprises at least one functional group protected by a protecting group, the protecting group being an acylation or an acetylation of the amino-terminal end, or an amidation or an esterification of the carboxy-terminal end, or both.

4. The composition according to claim 1, wherein the peptide consists of one of the following sequences:

Ile-Arg-Leu-Arg-Phe-Leu-Arg; (SEQ ID NO: 4)

```
                            (SEQ ID NO: 5)
Ile-Arg-Leu-Arg-Phe-Leu-Arg-NH2;

(SEQ ID NO: 6)
Ile-Lys-Leu-Arg-Phe-Leu-His;

(SEQ ID NO: 7)
Ile-Lys-Leu-Arg-Phe-Leu-His-NH2;

(SEQ ID NO: 8)
Ile-His-Leu-Lys-Phe-Leu-Arg;

(SEQ ID NO: 9)
Ile-His-Leu-Lys-Phe-Leu-Arg-NH2;
or (SEQ ID NO: 10)
Ile-Lys-Leu-His-Phe-Leu-Lys.
```

5. The composition according to claim 4, wherein the peptide consists of the sequence Ile-Arg-Leu-Arg-Phe-Leu-Arg (SEQ ID NO: 4).

6. The composition according to claim 4, wherein the peptide consists of the sequence Ile-Arg-Leu-Arg-Phe-Leu-Arg-NH₂ (SEQ ID NO: 5).

7. The composition according to claim 1, wherein the peptide is present in the composition at a concentration from 0.005 ppm to 500 ppm.

8. The composition according to claim 1, wherein the peptide is present in the composition at a concentration from 0.1 ppm to 50 ppm.

9. The composition according to claim 1, wherein said composition is in a form for topical cutaneous application comprising a pharmaceutically or cosmetically acceptable medium.

10. A method for the preparation of a cosmetic, dermatological, or pharmaceutical composition comprising adding a peptide according to claim 1 to a cosmetically or pharmaceutically acceptable carrier or excipient.

11. A method for treating skin against cutaneous aging comprising applying to the surface of the skin an effective quantity of the composition according to claim 7.

12. An isolated peptide of formula (I):

```
                            (SEQ ID NO: 1)
X1-Y-Phe-Thr-X2-Ala-Thr-Z-Ile-X3-Leu-X4-Phe-Leu-X5,
``` wherein
X1, X2, X3, X4, X5=Arg, Lys or His,
Y=Asp or Glu,
and Z=Asn or Gln;
or an isolated C terminal fragment of the peptide, consisting of 7 amino acid residues bearing a Phe-Leu motif of formula (II):
Ile-X3-Leu-X4-Phe-Leu-X5 (SEQ ID NO: 2), wherein
X3, X4, X5=Arg, Lys or His,
and optionally amidated at the C-terminal.

13. The peptide according to claim 12, wherein the peptide of formula (I) consists of the sequence Arg-Asp-Phe-Thr-Lys-Ala-Thr-Asn-Ile-Arg-Leu-Arg-Phe-Leu-Arg (SEQ ID NO: 3).

14. The peptide according to claim 12, wherein the peptide comprises at least one functional group protected by a protecting group, the protecting group being either an acylation or an acetylation of the amino-terminal end, or a amidation or an esterification of the carboxy-terminal end, or both.

15. The peptide according to claim 12, wherein the peptide consists of one of the following sequences:

```
(SEQ ID NO: 4)    Ile-Arg-Leu-Arg-Phe-Leu-Arg;
(SEQ ID NO: 5)    Ile-Arg-Leu-Arg-Phe-Leu-Arg-NH2;
(SEQ ID NO: 6)    Ile-Lys-Leu-Arg-Phe-Leu-His;
(SEQ ID NO: 7)    Ile-Lys-Leu-Arg-Phe-Leu-His-NH2;
(SEQ ID NO: 8)    Ile-His-Leu-Lys-Phe-Leu-Arg;
(SEQ ID NO: 9)    Ile-His-Leu-Lys-Phe-Leu-Arg-NH2;
or
(SEQ ID NO: 10)   Ile-Lys-Leu-His-Phe-Leu-Lys.
```

16. The peptide according to claim 15, wherein the peptide consists of the sequence Ile-Arg-Leu-Arg-Phe-Leu-Arg (SEQ ID NO: 4).

17. The peptide according to claim 15, wherein the peptide consists of the sequence Ile-Arg-Leu-Arg-Phe-Leu-Arg-NH₂ (SEQ ID NO: 5).

18. The peptide according to claim 12, wherein the peptide is present in the composition at a concentration from 0.005 ppm to 500 ppm.

19. The peptide according to claim 12, wherein the peptide is present in the composition at a concentration from 0.1 ppm to 50 ppm.

* * * * *